(12) United States Patent
Kinoshita et al.

(10) Patent No.: US 6,379,632 B1
(45) Date of Patent: Apr. 30, 2002

(54) ENDOSCOPE CLEANING AND DISINFECTING UNIT

(75) Inventors: Toshiharu Kinoshita, Hino; Mikihiko Nakagawa, Hachioji, both of (JP)

(73) Assignee: Olympus Optical Co., Ltd., Tokyo (JP)

( * ) Notice: Subject to any disclaimer, the term of this patent is extended or adjusted under 35 U.S.C. 154(b) by 0 days.

(21) Appl. No.: 09/497,994

(22) Filed: Feb. 4, 2000

(30) Foreign Application Priority Data

Feb. 5, 1999 (JP) .............................................. 11-28863

(51) Int. Cl.[7] ................................................. A61L 2/00
(52) U.S. Cl. .......................... 422/300; 422/28; 422/292; 222/65; 134/170; 134/171
(58) Field of Search ............................. 422/300, 37, 28, 422/292; 222/65

(56) References Cited

U.S. PATENT DOCUMENTS 4,391,287 A * 7/1983 Konoshima .................. 134/99
4,731,222 A * 3/1988 Kralovic et al. ............... 422/37
4,821,921 A * 4/1989 Cartwright et al. ........... 222/65

FOREIGN PATENT DOCUMENTS

| EP | 0 332 310 B1 | 2/1989 | ........... B65D/77/22 |
| EP | 0 543 591 A1 | 11/1992 | ............. A61L/2/18 |
| JP | 03176022 A | * 7/1991 | |

* cited by examiner

Primary Examiner—Robert J. Warden, Sr.
Assistant Examiner—Sean E. Conley
(74) Attorney, Agent, or Firm—Kenyon & Kenyon (57) ABSTRACT

An endoscope cleaning and disinfecting unit has an inlet arranged on its disinfectant solution tank through which a concentrated disinfectant solution is injected into the disinfectant solution tank. A diluting solution supply supplies a diluting solution for diluting the concentrated solution to the disinfectant solution tank and a plurality of level sensors detect the quantity of the disinfectant solution held in the disinfectant solution tank in stages. A control section controls the diluting solution supply based on the information detected by the level sensors to dilute the concentrated solution injected into the disinfectant solution tank through the inlet to a predetermined concentration.

19 Claims, 9 Drawing Sheets

ENDOSCOPE CLEANING AND DISINFECTING UNIT

BACKGROUND OF THE INVENTION

1. Field of the Invention

The present invention relates to an endoscope cleaning and disinfecting unit for cleaning and disinfecting an endoscope.

2. Description of the Related Art

Traditionally, endoscopes have been widely used for examination or treatment of a body cavity. An endoscope includes a variety of ducts for air supply, water supply, aspiration, etc. Its external surface and internal ducts must be cleaned and disinfected after each use.

Traditionally, various types of endoscope cleaning and disinfecting units have been used to clean and disinfect endoscopes. In principle, however, an endoscope is cleaned and disinfected in a cleaning tank through a series of processes constituted of cleaning the endoscope with cleaning water, disinfecting the cleaned endoscope with a disinfectant solution, rinsing, and drying.

During the above-mentioned disinfecting process, a pre-determined disinfectant solution is supplied to the cleaning tank from a disinfectant solution tank arranged within the unit. A pre-determined quantity of disinfectant and sterilizing solution (hereinafter simply referred to as "disinfectant solution") is stored in the disinfectant solution tank in advance. The disinfectant solution stored in the disinfectant solution tank is produced by diluting a concentrated disinfectant solution with diluting water. Traditionally, a disinfectant solution is prepared in a specific preparation place such as a sink by the user. And the prepared disinfectant solution is injected into the disinfectant solution tank from the inlet of the disinfectant solution tank by the user.

In the traditional case in which a disinfectant solution is prepared in a specific preparation place by the user, it is not easy to prepare a predetermined concentration of the disinfectant solution.

BRIEF SUMMARY OF THE INVENTION

The present invention addresses the above-mentioned problems.

A first aspect of the present invention is directed to an endoscope cleaning and disinfecting unit including a cleaning tank in which an endoscope to be cleaned is placed, a disinfectant solution tank in which a disinfectant solution to be supplied is held, and a disinfectant solution duct, connecting the disinfectant solution tank to the cleaning tank, through which a disinfectant solution flows between the cleaning tank and the disinfectant solution tank. The endoscope cleaning and disinfecting unit comprises an inlet arranged on the disinfectant solution tank through which a concentrated disinfectant solution is injected into the disinfectant solution tank, diluting solution supplying means for supplying a diluting solution for diluting the concentrated solution to the disinfectant solution tank a plurality of level sensors which detect the quantity of the disinfectant solution held in the disinfectant solution tank in stages, and means for controlling the diluting solution supplying means based on the information detected by the level sensors to dilute the concentrated solution injected into the disinfectant solution tank through the inlet to a predetermined concentration.

A second aspect of the present invention is an endoscope cleaning and disinfecting unit including a cleaning tank in which an endoscope to be cleaned is placed, a disinfectant solution tank in which a disinfectant solution to be supplied is held, and a disinfectant solution duct, connecting the disinfectant solution tank to the cleaning tank, through which the disinfectant solution flows between the cleaning tank and the disinfectant solution tank, wherein the disinfectant solution tank is provided with a bottle attaching section having a bottle receiving section for watertight reception of a closed mouth section of a bottle holding a concentrated disinfectant solution; an inlet for guiding the concentrated disinfectant solution into the disinfectant solution tank; and means for communicating the inside of the bottle with the inside of the disinfectant solution tank via the inlet by opening the mouth section of the bottle which is in watertight contact with the bottle receiving section.

A third aspect of the present invention is an endoscope cleaning and disinfecting unit including a cleaning tank in which an endoscope to be cleaned is placed, a disinfectant solution tank in which a disinfectant solution to be supplied is held, and a disinfectant solution duct, connecting the disinfectant solution tank to the cleaning tank, through which a disinfectant solution flows between the cleaning tank and the disinfectant solution tank. The endoscope cleaning and disinfecting unit comprises a bottle attaching section having a bottle receiving section which receives a closed mouth section of a bottle holding a concentrated disinfectant solution in a watertight and airtight manner, an inlet for guiding the concentrated disinfectant solution into the disinfectant solution tank, and means that allow the inside of the bottle to communicate with the inside of the disinfectant solution tank via the inlet by opening the mouth section of the bottle which is in watertight contact with bottle receiving section, diluting solution supplying means for supplying a diluting solution for diluting the concentrated solution to the disinfectant solution tank, a plurality of level sensors which detect the quantity of the disinfectant solution held in the disinfectant solution tank in stages, and means for controlling the diluting solution supplying means based on the information detected by the level sensors to dilute the concentrated solution injected into the disinfectant solution tank through the inlet to a predetermined concentration.

A fourth aspect of the present invention is an endoscope cleaning and disinfecting unit including a cleaning tank in which an endoscope to be cleaned is placed, a disinfectant solution tank in which a disinfectant solution to be supplied is held, and a disinfectant solution duct, connecting the disinfectant solution tank to the cleaning tank, through which a disinfectant solution flows between the cleaning tank and the disinfectant solution tank. The endoscope cleaning and disinfecting unit comprises a bottle attaching section having a bottle receiving section which receives a closed mouth section of a bottle holding a concentrated disinfectant solution in a watertight and airtight manner; an inlet for guiding the concentrated disinfectant solution into the disinfectant solution tank; and means that allow the inside of the bottle to communicate with the inside of the disinfectant solution tank via the inlet by opening the mouth section of the bottle which is in watertight contact with the bottle receiving section, diluting solution supplying means for supplying a diluting solution for diluting the concentrated solution to the disinfectant solution tank, a bottle detecting means for detecting the bottle being connected to the bottle attaching section, means for controlling the diluting solution supplying means based on the information detected by the bottle detecting means to dilute the concentrated solution injected into the disinfectant solution tank through the inlet to a predetermined concentration.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION

Referring to drawings, an embodiment of the present invention is described below.

Figure 1:
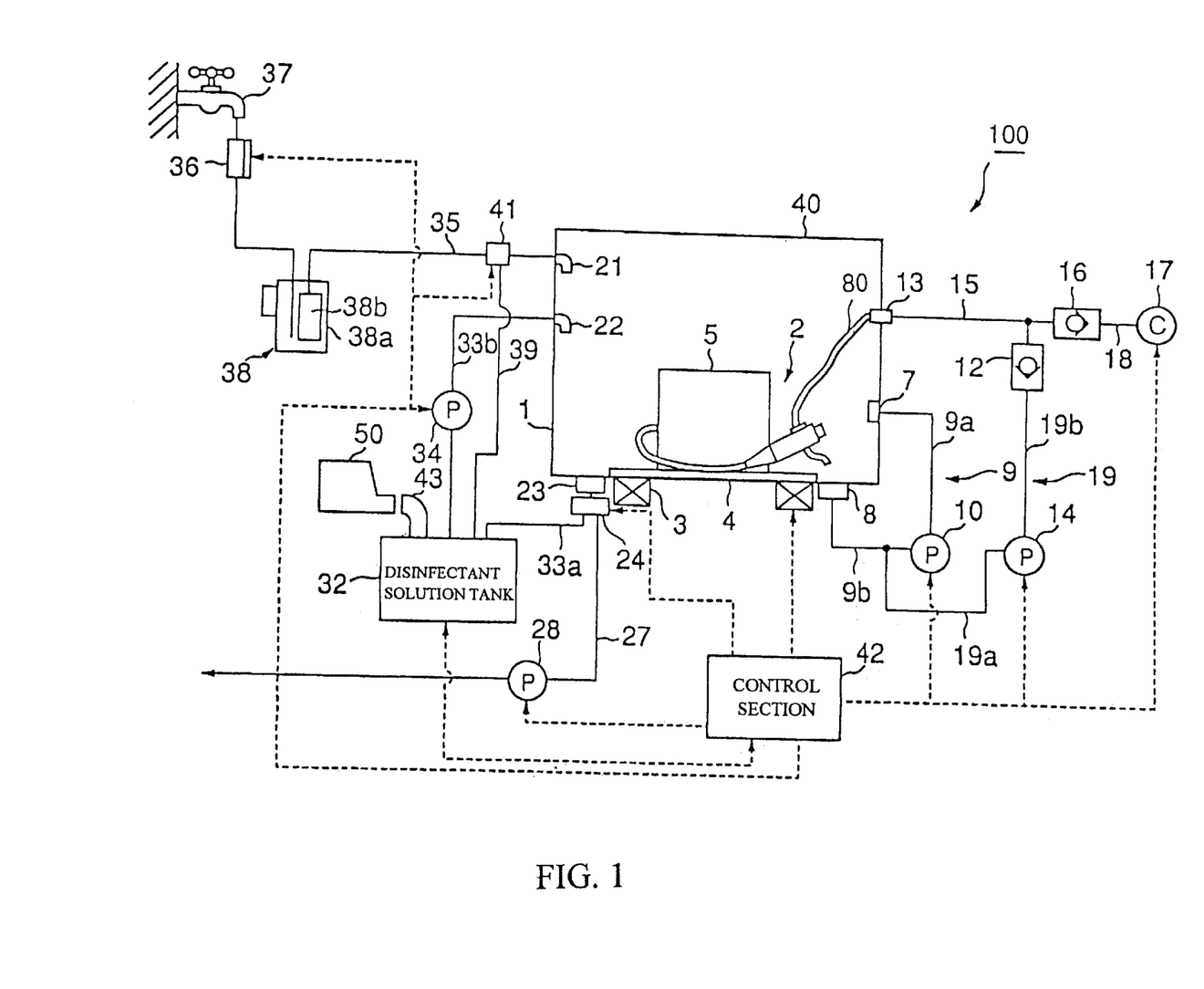
FIG. 1 is a schematic diagram of the endoscope cleaning and disinfecting unit according to an embodiment of the present invention.

FIG. 1 shows a rough configuration of the endoscope cleaning and disinfecting unit 100. As shown in FIG. 1, the endoscope cleaning and disinfecting unit 100 has a cleaning tank 1 forming its cleaning space: the endoscope 2 can be cleaned and disinfected in the cleaning tank 1. The cleaning tank 1 is provided with a lid 40 forming the top face of the cleaning space that can be opened or closed. Opening the lid 40, the endoscope 2 can be placed in the cleaning tank 1.

A diaphragm 4 is arranged at the bottom of the cleaning tank 1. The diaphragm 4 is, for example, provided with a Langevin-type ultrasonic oscillator 3 to produce oscillations in the cleaning solution held in the cleaning tank 1.

At the center of the bottom of the cleaning tank 1, is arranged a tower 5 to reduce the quantity of solution in the cleaning tank 1. A heater is arranged in the tower 5 to heat the solution in the cleaning tank 1.

The cleaning tank 1 is provided with a cleaning water inlet 21. To the cleaning water inlet 21, is connected a water duct 35 connected to a faucet 37 of the water source, for example, city water, so that cleaning water can be supplied into the cleaning tank 1 through the water duct 35. A water feed valve 36 and a standard water filter for sterilization 38 are arranged in the water duct 35. The water filter 38 is detachably fitted in the filter receiving space within the body of the cleaning and disinfecting unit, comprising a water filter housing 38a and a disposable filter cartridge 38b detachably placed in the housing 38a.

A cleaning solution spout 7 is disposed on a sidewall of the cleaning tank 1, and a circulating solution suction mouth 8 is arranged at the bottom of the cleaning tank 1. To the cleaning solution spout 7, is connected a first solution supply duct 9a connected to the discharge side of the first solution supply pump 10, while a second solution duct 9b, connected to the suction side of the first solution supply pump 10, is connected to the circulating solution suction mouth 8. The first and second solution supply ducts 9a and 9b form the first circulatory route 9 through which the solution recovered from the cleaning tank 1 can be pressurized to the cleaning tank 1 again.

On a sidewall of the cleaning tank 1, is arranged a channel connection mouth 13 to which a connection tube 80 is connected. In this case, the connection tube 80 is detachably connected to the connection mouth section that communicates with the internal channel arranged in the operation section of the endoscope 2.

The third solution supply duct 19a branches from the second solution supply duct 9b, and is connected to the suction side of the second solution supply pump 14. To the second solution supply pump 14, is connected the forth solution supply duct 19b. The forth solution supply duct 19b is connected to the fluid supply duct 15 connected to the channel connection mouth 13 via a check valve 12. That is, the third and forth solution supply ducts 19a and 19b form the second circulatory route 19 through which the solution recovered from the cleaning tank 1 can be pressurized to the cleaning tank 1 again through the internal channel of the endoscope 2.

A air supply duct 18 is connected to the midway point of the fluid supply duct 15 via a check valve 16. A compressor 17 is connected to the air supply duct 18 so that compressed air from the compressor 17 can be supplied to the fluid supply duct 15 through the air supply duct 18.

A disinfectant solution inlet 22 is arranged on a sidewall of the cleaning tank 1, and a discharge opening 23 is arranged at the bottom of the cleaning tank 1. To the disinfectant solution inlet 22, is connected a disinfectant solution supply duct 33b connected to the disinfectant solution tank 32 to supply the disinfectant solution from the disinfectant solution tank 32 to the cleaning tank 1 by the suction of the pump 34. A disinfectant solution return duct 33a and a discharge duct 27 are connected to the duct extending from the discharge opening 23 via a duct switching valve 24. The disinfectant solution return duct 33a is connected to the disinfectant solution tank 32 to recover the disinfectant solution from the cleaning tank 1 to the disinfectant solution tank 32. From the disinfectant solution tank 32, extends a diluting solution supply duct 39 that is connected to the midway of the water duct 35 via a duct switching valve 41. That is, in the present embodiment, the duct switching valve 41 and the diluting solution supply duct 39 constitute a diluting solution supply means to supply the cleaning water flowing in the water duct 35 to the disinfectant solution tank 32 as a diluting solution.

A discharge pump 28 is arranged in the discharge duct 27. All of the ultrasonic oscillator 3, pumps 10, 14, 28, and 34, compressor 17, and duct switching valves 24 and 41, and water feed valve 36 are controlled by a control section 42. For example, the control section 42 is a kind of microprocessor in a computer which is included in the endoscope cleaning and disinfecting unit.

Next, the bottle section 50 detachably attached to the disinfectant solution tank 32 and the disinfectant solution tank 32 will be described in more detail.

Figure 2:
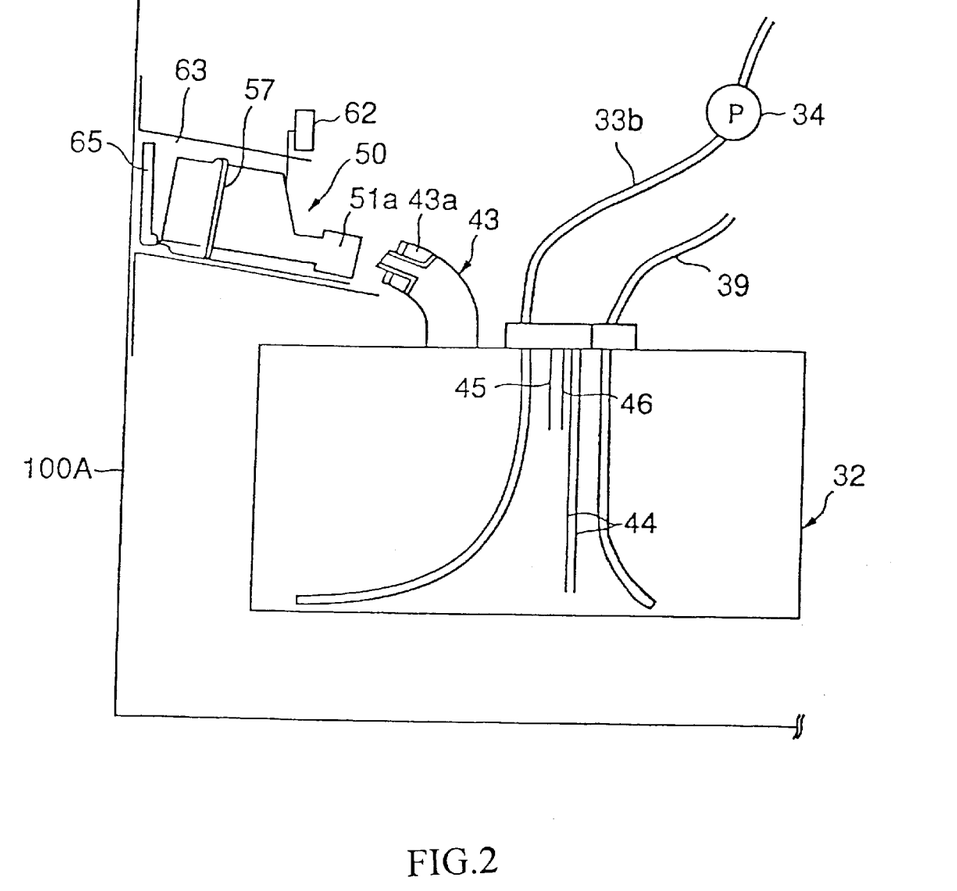
FIG. 2 is a schematic diagram of the disinfectant solution tank, a key part of the endoscope cleaning and disinfecting unit shown in FIG. 1.

As shown in FIG. 2, the disinfectant solution tank 32 is disposed in the body 100A of the cleaning and disinfecting unit 100. On the upper face of the disinfectant solution tank 32, is arranged a mouthpiece-like bottle attaching sections 43 to which the bottle section 50 holding a concentrated disinfectant solution is detachably attached. The bottle attaching section 43 has a curved upper portion so that the opening section is oriented in the lateral direction.

Figures 3A, 3B:
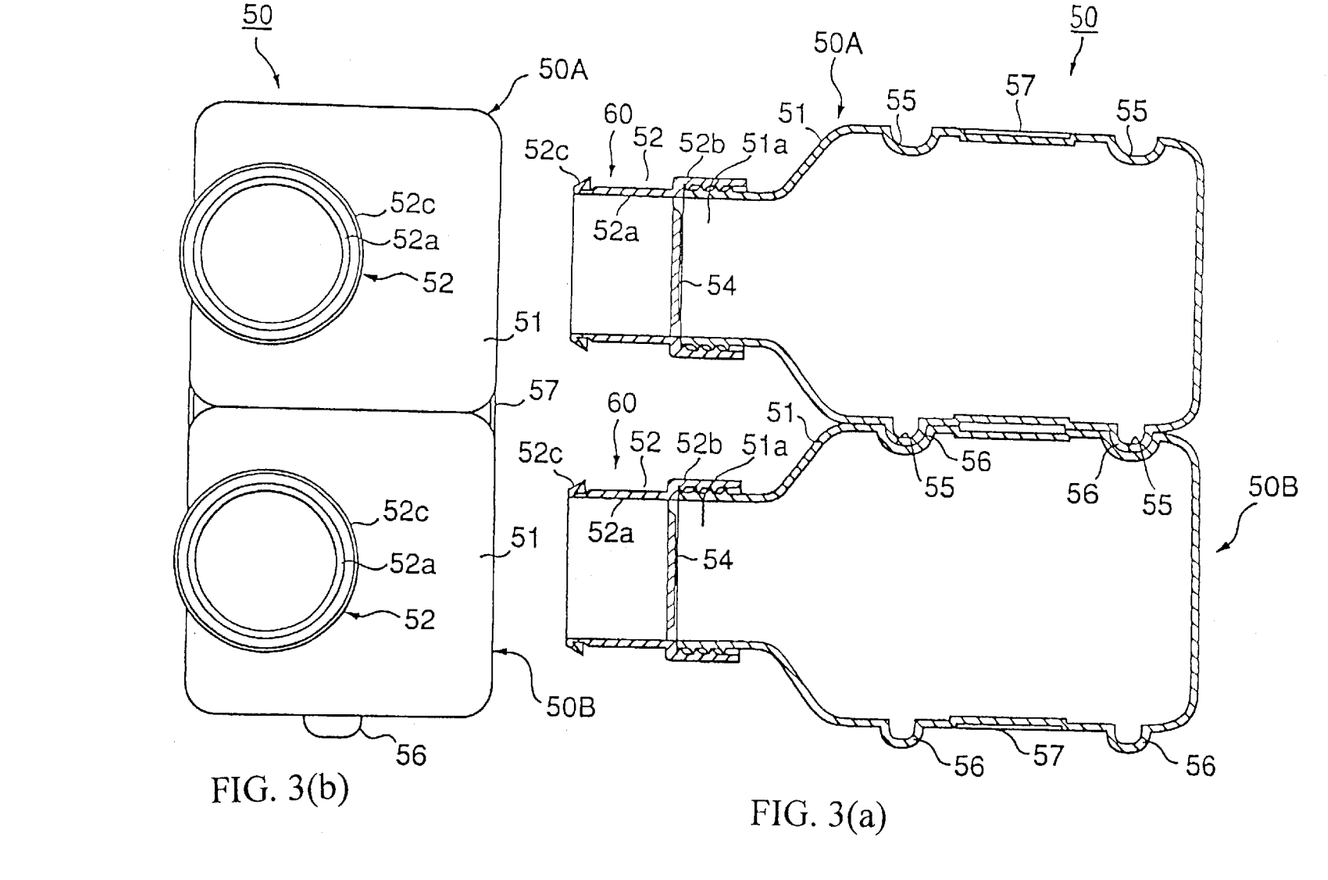
FIG. 3(a) is a cross-sectional view of the bottle to be attached to the disinfectant solution tank shown in FIG. 2.
FIG. 3(b) shows a front view of the mouth section of the bottle shown in FIG. 3(a).

As shown in more detail in FIG. 3, the bottle section 50 attached to the bottle attaching section 43 comprises a first bottle 50A holding a main concentrated solution and a second bottle 50B holding a buffer. Each of the bottles 50A and 50B comprises a bottle-like bottle body 51 in which a solution is stored and a cap 52 which is attached to the mouth section 51a of the bottle body 51. The mouth sections 51a are eccentric to the center axis of the bottle body 51 so that even when the bottles 50A and 50B lie on their side (as shown in FIG. 2), solutions held in the bottles 50A and 50B may be completely discharged through the mouth sections 51a due to their own weight. Specifically, the mouth sections 51a are located on the outer circumference of the bottle body 51 so that the inner face of a sidewall of the bottle body 51 may be on the same plane as the inner face of the mouth sections 51a.

Each of the caps 52, which comprises a cylinder-like cap body 52a, an attachment section 52b formed at the proximal end of the cap body 52a and attached to the bottle body 51, and a sealing section 52c formed at the distal end of the cap body 52a and constituted of an elastic-material member protruding outwardly on the radial direction of the cap 52, constitutes a detachable section 60 detachably attached to a bottle attaching section 43 on the side of the disinfectant solution tank 32. In addition, a cap 52 has a resin film (not renewable once ruptured) that is located at the boundary between the attachment section 52b and the cap body 52a, and can close off the mouth section 51a when the cap 52 is attached to the mouth section 51a of the bottle body 51 via the attachment section 52b.

On a sidewall of the bottle body 51, is arranged a pair of concave sections 55 along the longitudinal axis of the bottle body 51. On another sidewall of the bottle body 51, is arranged a pair of convex sections 56 along the longitudinal axis of the bottle body 51. The first bottle 50A and the second bottle 50B are integrally assembled without longitudinally deviating from each other by engaging the concave sections 55 on a sidewall with the convex sections 56 on another sidewall. In this case, the mouth sections 51a (cap 52) of the bottles 50A and 50B are oriented so that they may be side by side as shown FIG. 3(b). Such an assembled condition is firmly maintained by a shrink film 57, that integrally winds around the sidewalls of the bottles 50A and 50B, to thereby form the bottle section 50. Such an assembled condition may be also maintained by welding the bottles 50A and 50B to each other without a shrink film 57.

Each bottle section 50 is detachably attached to the bottle attaching section 43 from which a concentrated disinfectant solution can be injected into the disinfectant solution tank 32. As shown in FIG. 4, the bottle attaching section 43 has the bottle receiving section 43a for receiving the mouth section 51a of the bottle 50A. Likewise the bottle 50B also includes a mouth receiving section 51a. The bottle attaching section 43 and the mouth section 51a along with the cap 52 form an airtight and watertight seal. An inlet 43c guides the concentrated solution into the disinfectant solution tank 32, and a pair of protruding sections 43b allow the insides of the bottles 50A and 50B to communicate with the inside the disinfectant solution tank 32 by opening the mouth sections 51a of the bottles 50A and 50B while the mouth section 51a of the bottles 50A and 50B are in watertight contact with the bottle receiving sections as shown in FIG. 3(c).

A bottle receiving section 43a has a two-tube structure comprising an external tube a and an internal tube b arranged in a coaxial manner. In this case, the ring-shaped space between the external tube a and the internal tube b is set for the measurement obtained by fitting the caps 52 of the bottles 50A and 50B, for example, almost the same as the thickness of the cap body 52a. A protruding section 43b is disposed inside the internal tube b, its end face being tapered, and its internal hole communicating with the inlet 43c.

As shown in FIG. 2, a plurality of level sensors 44, 45, and 46 are arranged in the disinfectant solution tank 32 for detecting the quantity of the solution stored in the disinfectant solution tank 32 in stages. The first level sensor 44 can detect the predetermined quantity of a concentrated solution to be injected into the disinfectant solution tank 32 via the concentrated solution bottles 50A and 50B. The second level sensor 45 can detect the quantity of diluting solution to be supplied for diluting the predetermined quantity of the concentrated solution injected into the disinfectant solution tank 32 (actually, the quantity of the entire disinfectant solution of the predetermined concentration including the diluting solution and the concentrated solution already injected into the tank 32). The third level sensor 46 can detect the minimum quantity required to raise the disinfectant solution to the cleaning tank located in the upper side when starting the unit (the minimum quantity of the disinfectant solution required to appropriately disinfect the endoscope 2 in the cleaning tank 1). Information detected by the level sensors 44, 45, and 46 is transmitted to the control section 42.

As shown in FIG. 2, on a sidewall of the unit body 100A, is formed a bottle insertion hole section 63 into which the bottle section 50 is inserted, and which is tilted with an inclination to the obliquely downward direction. Since the bottle section 50 can be attached to the disinfectant solution tank 32 from a side of the unit in such a way, the cleaning and disinfecting unit 100 in which a lot of elements are arranged on the disinfectant solution tank 32 may be reduced in size.

Facing the internal end opening of the bottle insertion hole 63, are the upper end sections of the laterally curved bottle attaching sections 43. In this case, the bottle receiving sections 43a of the bottle attaching sections 43 are located at a lower part in the bottle insertion hole 63. That is, when the bottles 50A and 50B are set in the bottle insertion hole 63 with their mouth sections 51a down as shown in FIG. 2. In this position, the mouth sections 51a (cap 52) can be attached to the bottle receiving sections 43a. However, when the bottles 50A and 50B are set in the bottle insertion hole 63 with the mouth sections 51a up, the mouth sections 51a (cap 52) cannot be attached to the bottle receiving sections 43a. Accordingly, the bottle section 50 is prevented from being reversed.

Figure 4A:
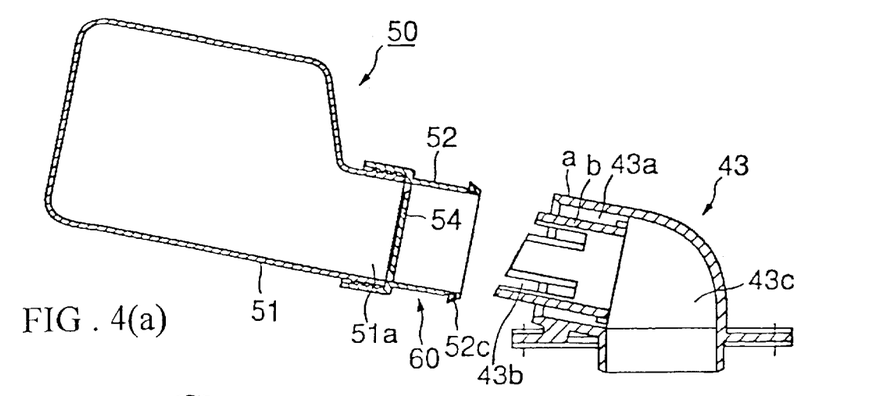
FIG. 4 is a sectional view of the attachment section of the bottle and the disinfectant solution tank.
Figure 4B:
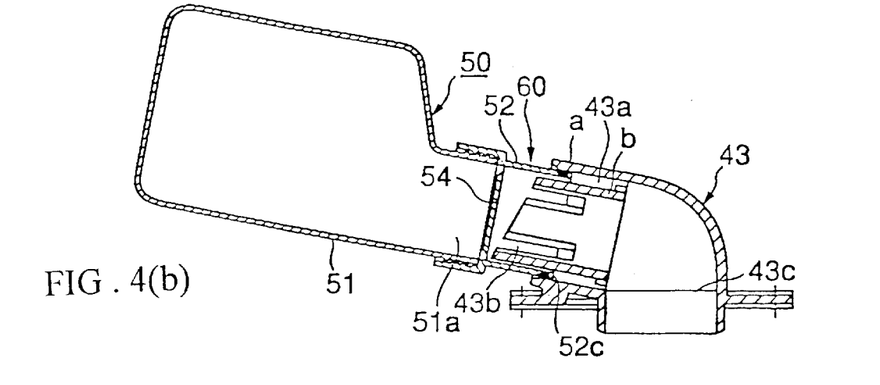
Figure 4C:
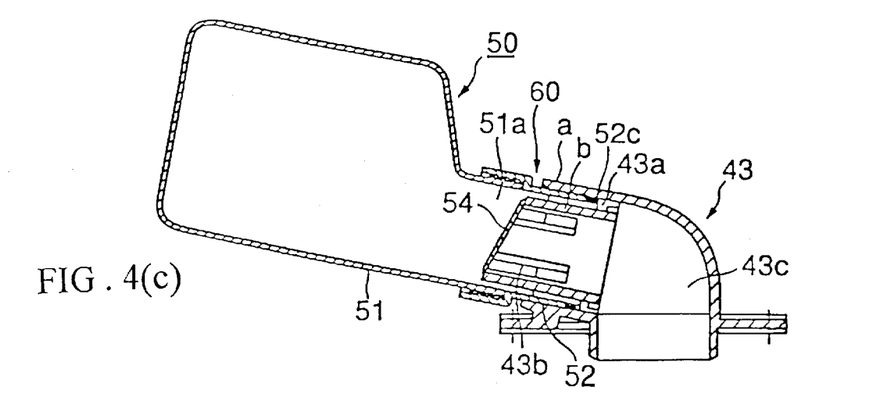

A bottle detecting sensor 62 is arranged in the bottle insertion hole 63 to detect the bottles 50A and 50B being appropriately connected to the bottle attaching sections 43. The bottle detecting sensor 62 is actuated when it comes into contact with the bottle section 50 at the position, as shown in FIG. 4(c), at which the bottles 50A and 50B are appropriately connected to the bottle attaching sections 43. Moreover, when the bottles 50A and 50B are appropriately connected to the bottle attaching sections 43, the bottle section 50 completely disappears into the bottle insertion hole 63. Information detected by the bottle detecting sensor 62 is transmitted to the control section 42.

Figure 5A:
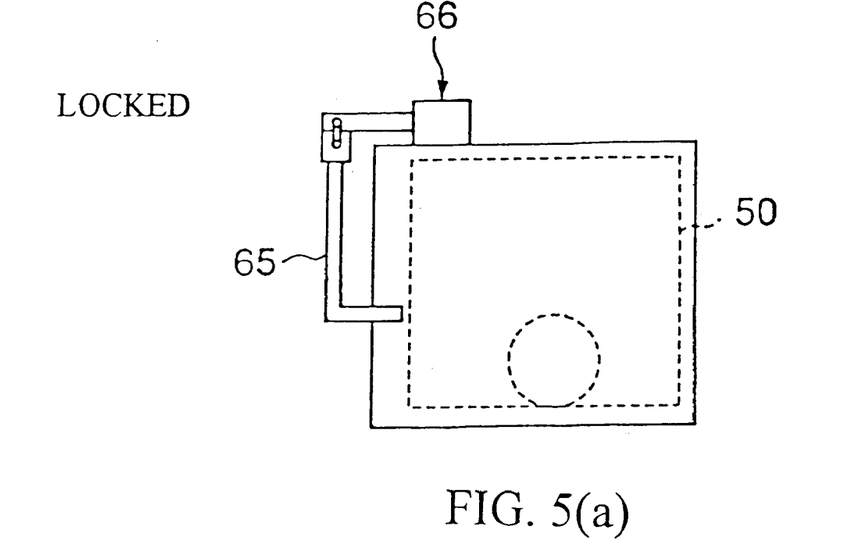
FIG. 5(a) is a view showing the bottle locked to the attachment section of the disinfectant solution section by the lock device.
Figure 5B:
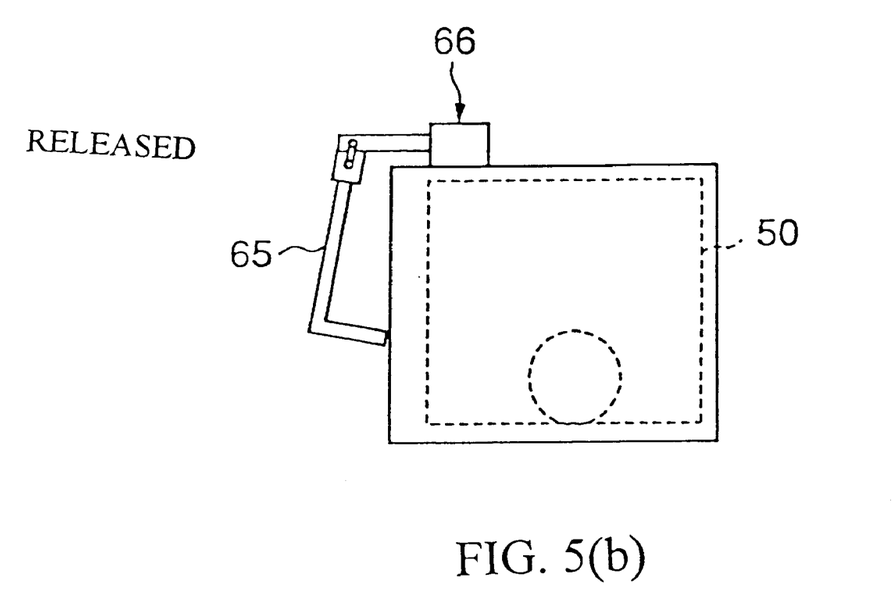
FIG. 5(b) is a view showing the lock device released.

As shown in FIGS. 2 and 5, a lock device 66 is also arranged in the bottle insertion hole 63 to lock the bottle section 50 at the position, as shown in FIG. 4(c), at which the bottles 50A and 50B are appropriately connected to the bottle attaching sections 43. The lock device 66 has a lock arm 65 for supporting the bottom face of the bottle section 50 to prevent the bottle section 50 from coming off from the bottle insertion section 63.

Next, referring to the flow chart in FIGS. 6 through 9, an explanation will be given for how a concentrated disinfectant solution injected into the disinfectant solution tank 32 of the above-mentioned endoscope cleaning and disinfecting unit 100 is automatically diluted.

Figure 6:
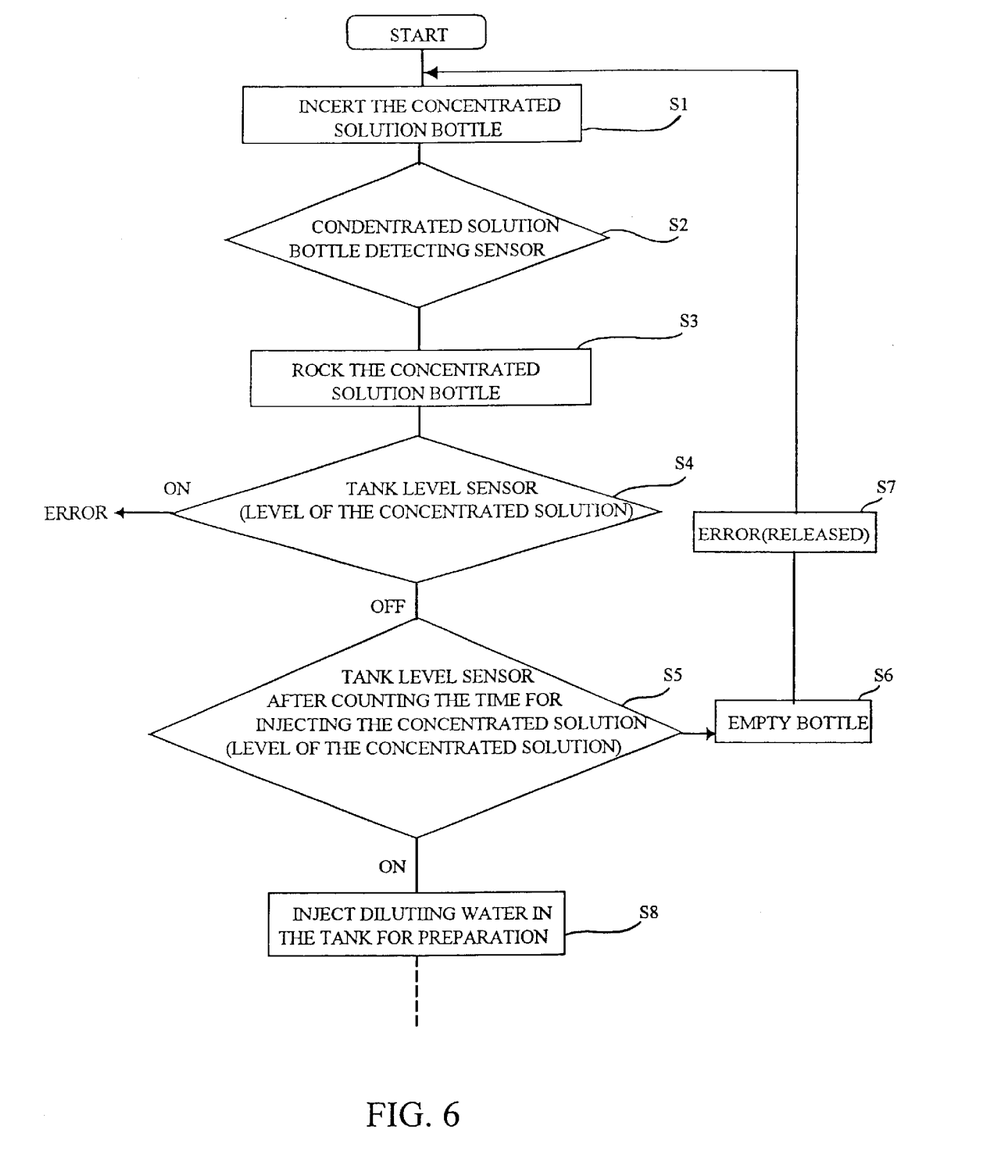
FIG. 6 is a basic flow chart which shows how the concentrated disinfectant solution injected into the disinfectant solution tank is diluted.
Figure 8:
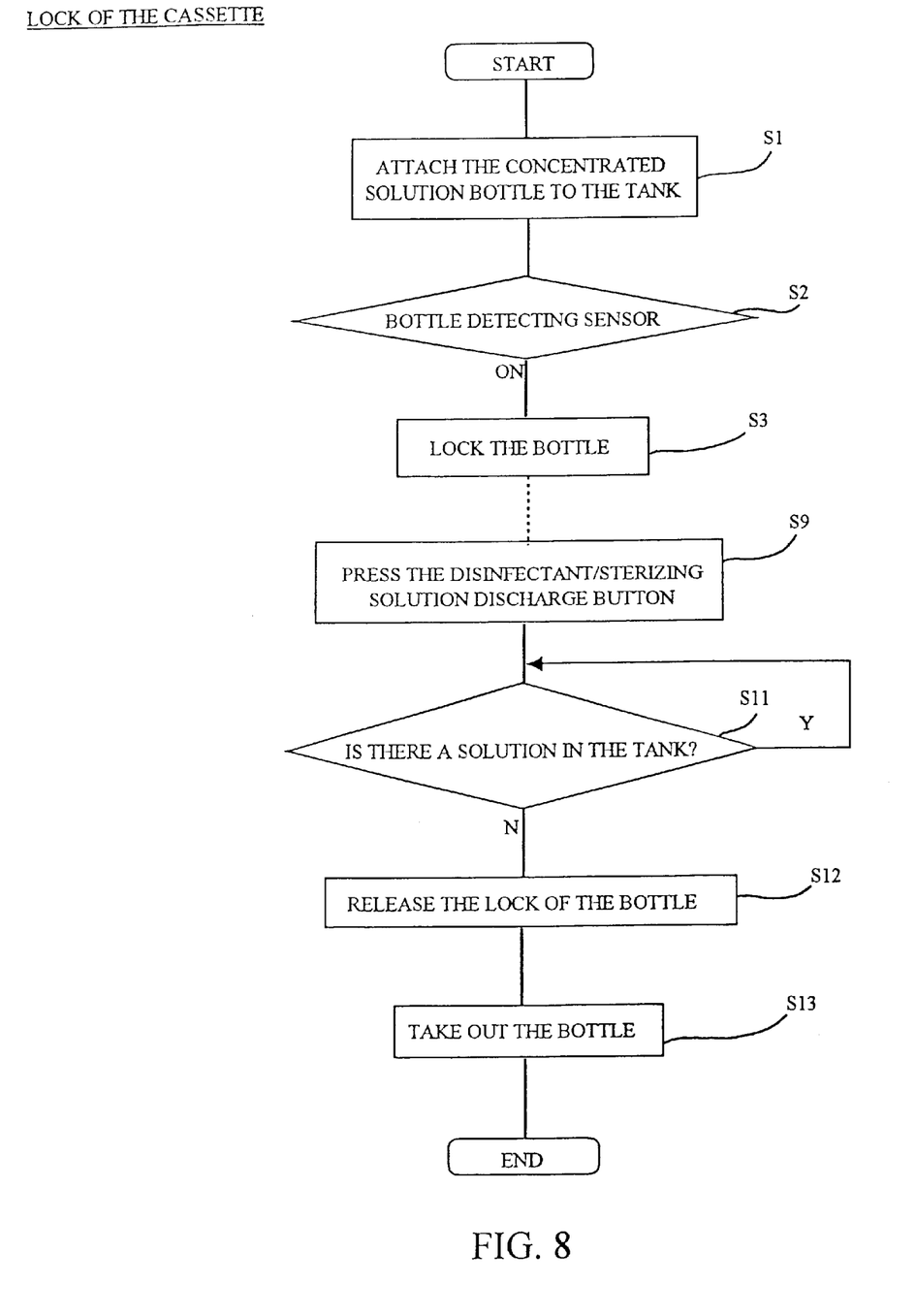
FIG. 8 is a flow chart which shows how the lock device operates.

First, insert the bottle section 50 (holding a concentrated disinfectant solution in it) into the bottle insertion hole 63. The mouth sections 51a of the bottles 50A and 50B are closed off by the film sections 54 with the mouth sections down (FIGS. 6 and 8-S1). As shown in FIG. 4(a), the caps of the bottles 50A and 50B face the bottle receiving sections 43a of the bottle attaching sections 43 on the side of the disinfectant solution tank 32. Next, when the bottle section 50 is further pushed into the bottle insertion hole 63, the cap bodies 52a of the caps 52 of the bottles 50A and 50B can be fitted to the ring-shaped space between the external tube a and the internal tube b, and the closed off mouth sections 51a of the bottles 50A and 50B can be received by the bottle receiving sections 43a. In this case, the sealing section 52c is pressed by the inner face of the external tube a, and is elastically deformed to maintain the mouth sections 51a watertight to the outside(See FIG. 4(b)). When the bottle section 50 is further pushed into the bottle insertion hole 63, the film sections 54 can be ruptured by the protruding sections 43b, and the mouth sections 51a can be opened while the mouth sections 51a are received in watertight fashion as shown in FIG. 4(c). This allows the inside of the bottles 50A and 50B to communicate with the inside of the disinfectant solution tank 32 via the injection port 43c, and the solution in the bottles 50A and 50B can be completely injected into the disinfectant solution tank 32 because of the shape of the bottles 50A and 50B.

When the bottle section 50 is completely connected to the bottle attaching sections 43 in such a way, the bottle detecting sensor 62 comes into contact with the bottle section 50, and is actuated (FIGS. 6 and 8-S2). The detected information is transmitted to the control section 42, and the control section 42 actuates the lock device 66 based on the detected information. This allows the lock arm 65 to support the bottom face of the bottle section 50 (FIG. 5(a)), and prevents the bottle section 50 from coming off from the bottle insertion hole 63 (FIGS. 6 and 8-S3). At this moment, the control section 42 judges whether the first level sensor 44 is turned on or not (FIG. 6-S4). If it is turned on, the control section 42 determines that the disinfectant solution in the disinfectant solution tank 32 is not completely discharged. In this case, the control section 42 notifies the user of the error, and encourages him or her to discharge the disinfectant solution from the disinfectant solution tank 32.

If the bottle section 50 is locked by the lock device 66 and the first level sensor 44 is off, the control section 42 counts the time while the concentrated disinfectant solution is being injected from the bottle section 50 into the disinfectant solution tank 32 (FIG. 6-S5). And, if the first level sensor 44 cannot be turned on within the predetermined time, the control section 42 determines that an empty bottle section 50 has been placed in the bottle insertion section 63 (FIG. 6-S6). In this case, the control section 42 notifies the user of the error, and encourages him or her to release the lock device 66 and replace the bottle section 50.

On the other hand, if the first level sensor detects the predetermined quantity of the concentrated solution (the entire quantity of the solution held in the bottle section 50) having been injected into the tank 32 within a predetermined time, the control section 42 opens the water feed valve 36, and switches the duct switching valve 41 to connect the water duct 35 to the diluting solution supply duct 39. This allows cleaning water as a diluting solution to be injected into the disinfectant solution tank 32 (FIG. 6-S8). Then, when the concentrated solution is diluted by the diluting solution, and the quantity of the disinfectant solution is detected by the second level sensor 45, the control section 42 judges that the concentration of the disinfectant solution has attained the predetermined level, and stops supplying the diluting solution to the disinfectant solution tank 32.

Figure 7:
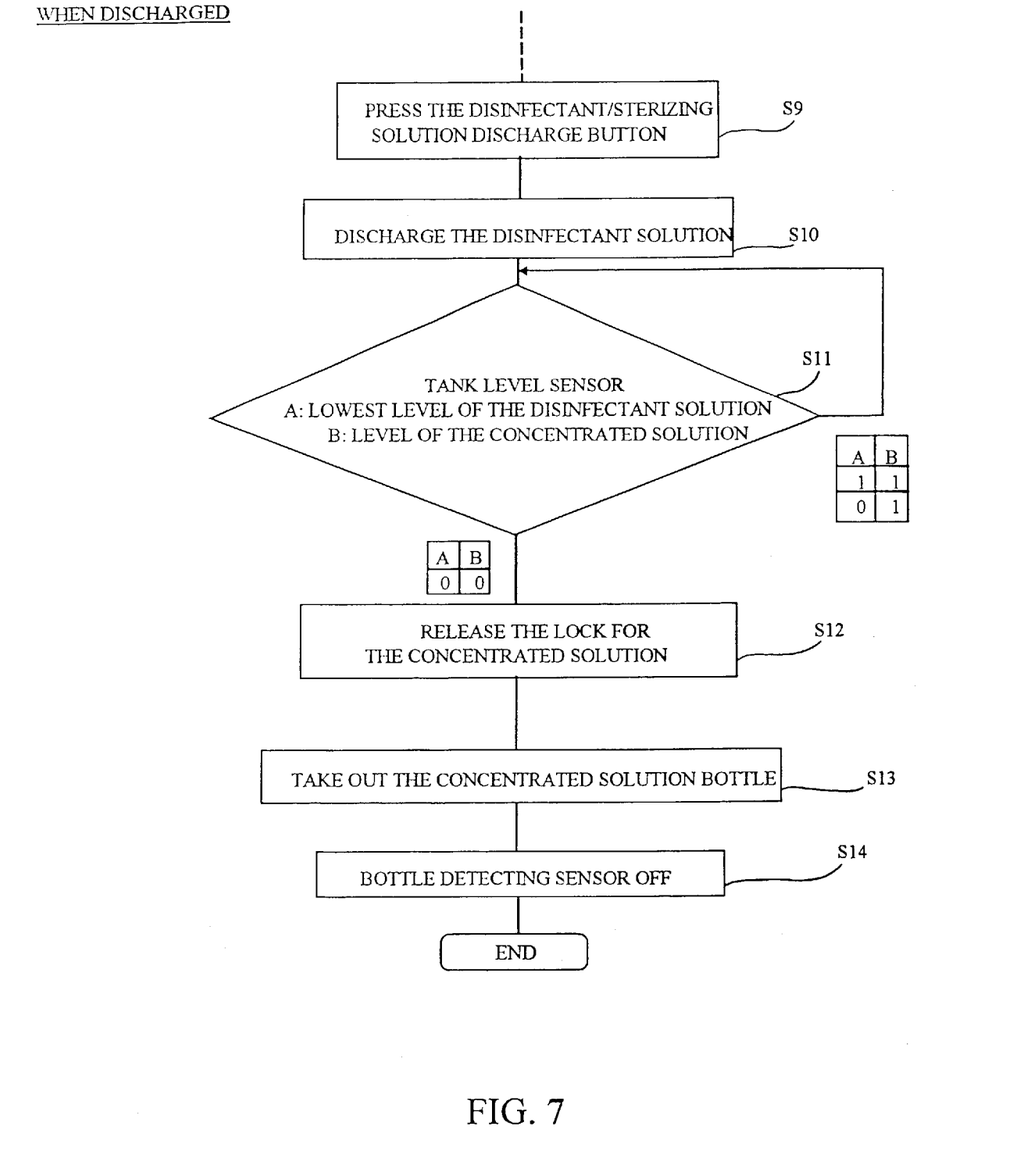
FIG. 7 is a flow chart which shows how the disinfectant solution is discharged from the disinfectant solution tank.

On the other hand, when the disinfectant solution in the disinfectant solution tank 32 is reduced to the predetermined quantity due to use of the disinfectant solution, the third level sensor 46 detects it. Then, the control section 42 encourages the user to discharge the disinfectant solution from the disinfectant solution tank 32. In this case, the user should press the discharge button (not illustrated) (FIGS. 7 and 8-S9) to discharge the disinfectant solution (FIG. 7-S10). After the disinfectant solution has been discharged, and the first level sensor 44 has been turned off (FIGS. 7 and 8-S11), the control section 42 judges that the disinfectant solution has been discharged, and releases the lock device 66 (FIGS. 7 and 8-S12). This allows the user to take out the bottle section 50 and replace it with another (FIGS. 7 and 8-S13). When the connection of the bottle section 50 and the bottle receiving sections 43a is released, the bottle detecting sensor 62 is also turned off (FIG. 7-S14).

Figure 9:
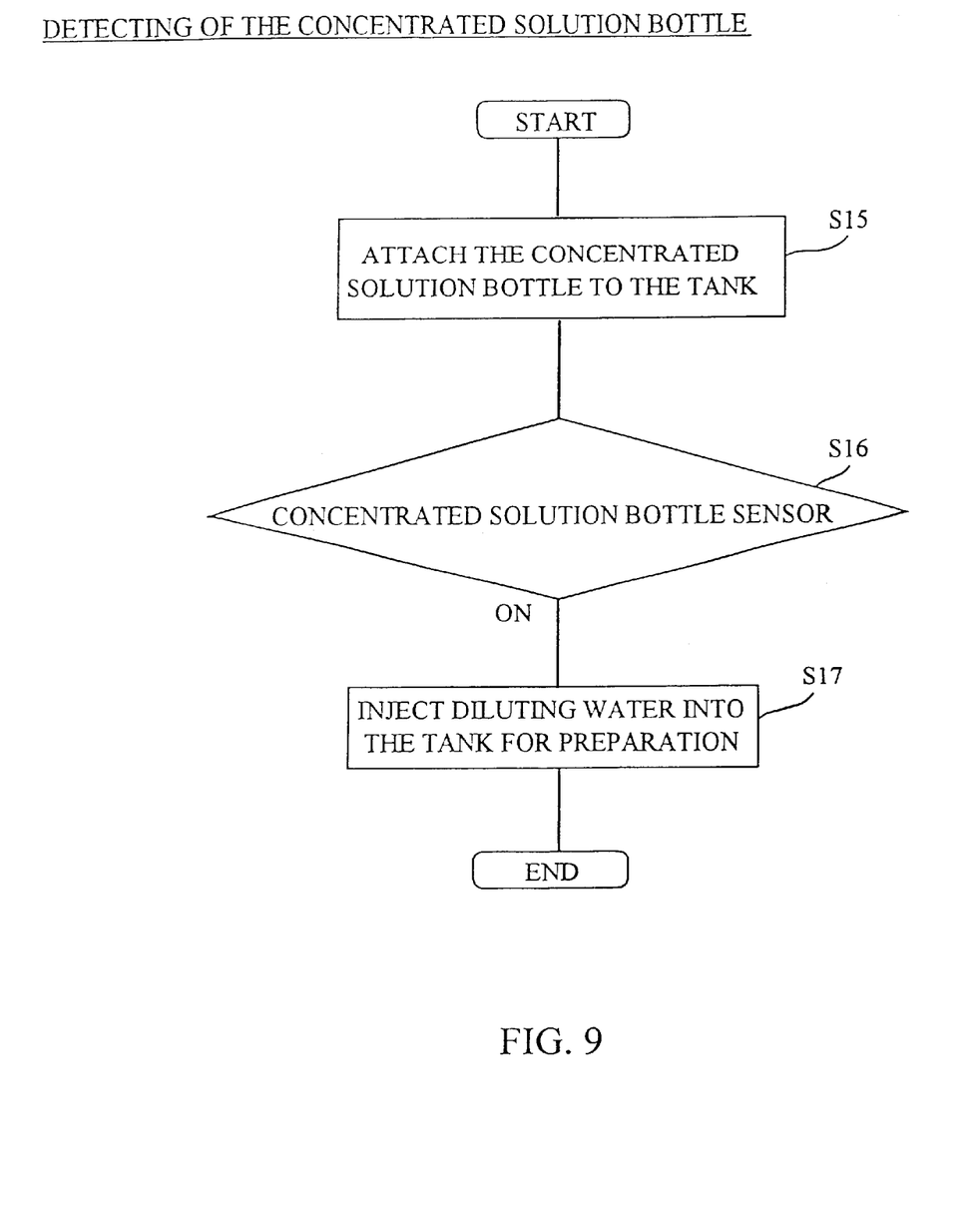
FIG. 9 is a flow chart which shows how dilution of the concentrated solution is controlled only through the information detected by the bottle detecting sensor.

As mentioned above, a concentrated solution can be diluted to a predetermined concentration by supplying a diluting solution to the disinfectant solution tank 32 based on the information detected by the level sensors 44, 45, and 46. However, it may be diluted based on the information detected by the bottle detecting sensor 62. As shown in the flowchart of FIG. 9, when the bottle detecting sensor 62 detects (FIG. 9-S16) the bottle section 50 having been connected to the bottle receiving sections 43a (FIG. 9-S15), the control section 42 opens the water feed valve 36, and switches the duct switching valve 41 to connect the water duct 35 to the diluting solution supply duct 39. This allows cleaning water as a diluting solution to be injected into the disinfectant solution tank 32 (FIG. 9-S17). Then, when the concentrated solution is diluted by the diluting solution, and the quantity of the disinfectant solution is detected by the second level sensor 45, the control section 42 judges that the concentration of the disinfectant solution has attained the predetermined level, and stops supplying the diluting solution to the disinfectant solution tank 32.

After a disinfectant solution has been automatically prepared through the above-mentioned processes, it becomes possible to clean and disinfect the endoscope 2 according to the following processes.

In order to clean and disinfect an endoscope 2 with the endoscope cleaning and disinfecting unit 100, place the used endoscope 2 in the cleaning tank 1, and connect the endoscope 2 and the channel connection port 22 with a connection tube 80. And, the processes for cleaning, disinfecting, rinsing, and supplying air can be automatically implemented through various switches.

In the cleaning process, the water feed valve 36 is opened first, cleaning water from the water source 37 is supplied from the cleaning water inlet 21 to the cleaning tank 1 through the water duct 35. Before the cleaning process, the user must put a predetermined quantity of detergent solution in the cleaning tank 1 in advance.

After a predetermined quantity of water is supplied to the cleaning tank 1, the water feed valve is closed, and the first and second solution supply pumps 10 and 14 are actuated. At this moment, the duct switching valve 24 is closed.

This allows a part of the cleaning solution in the cleaning tank 1 to be circulated through the first circulatory route 9 and sprayed on the outer surface of the endoscope 2 from the cleaning solution spout 7, and to be circulated through the second circulatory route 19 and supplied to the internal duct of the endoscope 2. That is, the cleaning solution in the cleaning tank is drawn from the circulating solution suction mouth 8 to the second solution supply duct 9b by suction of the first solution supply pump 10, and spouted (ejected) from the cleaning solution spout 7 through the first solution supply duct 9a. A part of the cleaning solution drawn into the second solution supply duct 9b is drawn into the third solution supply duct 19a by suction of the second solution supply pump 14, and supplied from the channel connection mouth 13 to the internal duct of the endoscope 2 through the forth solution supply duct 19b and the fluid supply duct 15. The cleaning solution supplied to the internal duct of the endoscope 2 is returned to the cleaning tank 1 through the end opening of the endoscope 2, and circulated again through the first circulatory route 9 or the second circulatory route 19.

Such a flow of the cleaning solution allows big, soft, or light dirt on the endoscope 2 to be washed off. Such dirt is removed from the outer face of the endoscope 2 particularly by the impact of the cleaning solution directed from the cleaning solution spout 7, or the swirling current generated in the cleaning tank 1 by it.

After cleaning by circulation of the cleaning solution is carried out for a predetermined time, the diaphragm 4 is actuated for ultrasonic cleaning. During the ultrasonic cleaning, hard dirt on the endoscope 2 or dirt in the complicated configuration of the endoscope 2 is powerfully eliminated by ultrasonic oscillation.

After ultrasonic cleaning, the above-mentioned cleaning by circulation of the cleaning solution is carried out again. During this stage, such dirt as is just peeling off the endoscope 2 can be removed by ultrasonic oscillation.

After the above-mentioned cleaning process is completed, the rinsing process starts. In the rinsing process, the solution supply pumps 10 and 14 are stopped first, and the discharge pump 28 is actuated, and the duct switching valve is switched for the discharge duct 27. This allows the cleaning solution in the cleaning tank 1 to be discharged from the discharge opening 23 through the discharge duct. After the cleaning solution in the cleaning tank 1 is completely discharged, the water feed valve 36 is opened to supply water anew to the cleaning tank 1. Then, the first and second solution supply pumps 10 and 14 are actuated again, and the internal duct and outer surface of the endoscope 2 are rinsed by the above-mentioned circulation.

Rinsing with water being finished, drainage is carried out after rinsing water is completely discharged from the cleaning tank 1. Before drainage, the solution supply pumps 10 and 14 are stopped, and the compressor 17 is actuated to supply air from the compressor 17 to the fluid supply duct 15 through the air supply duct 18. Air supplied to the fluid supply duct 15 is supplied to the internal duct of the endoscope 2 for drainage of the internal duct of the endoscope 2.

The above-mentioned rinsing process is followed by the disinfecting process. In the disinfecting process, the duct switching valve 24 is closed, and the pump 34 is actuated. This allows the disinfectant solution in the disinfectant solution tank 32 to be injected from the disinfectant solution inlet 22 into the cleaning tank 1 through the disinfectant solution supply duct 33b. After a predetermined quantity of disinfectant solution is injected into the cleaning tank, and the endoscope 2 is completely immersed in the disinfectant solution, the pump 34 is stopped, and then, the solution supply pump 14 is actuated. This allows the disinfectant solution in the cleaning tank 1 to be supplied to the internal duct of the endoscope 2 for disinfecting the internal duct of the endoscope 2.

After such disinfecting work is carried out for a predetermined time, the duct switching valve 24 is switched for the disinfectant solution return duct 33a, and the disinfectant solution in the cleaning tank 1 is recovered into the disinfectant solution tank 32 through the disinfectant solution return duct 33a. Then, the disinfectant solution is rinsed out through the above-mentioned rinsing process.

After the disinfectant solution is completed rinsed out through the rinsing process, the air supply process is carried out. The air supply process is carried out using the same procedure as with the drainage conducted in the latter half of the rinsing process. And, the discharge pump 28 is stopped after a predetermined time.

As mentioned above, the endoscope cleaning and disinfecting unit 100 according to the present embodiment has a bottle attaching section 43 arranged on the disinfectant solution tank 32 through which a concentrated disinfectant solution is injected into disinfectant solution tank 32; diluting solution supplying means 36, 39, and 41 for supplying a diluting solution for diluting the concentrated solution to the disinfectant solution tank 32, a plurality of level sensors 44, 45, and 46 which detect the quantity of the disinfectant solution stored in the disinfectant solution tank 32 in stages, and a control section 42 which controls the diluting solution supplying means 36, 39, and 41 based on the information detected by the level sensors 44, 45, and 46 to dilute the concentrated solution injected into the disinfectant solution tank 32 through the bottle attaching section 43 to a predetermined concentration.

Therefore, a predetermined concentration of a disinfectant solution can be exactly obtained, and the expected disinfecting results can be obtained because the disinfectant solution is automatically prepared in the endoscope cleaning and disinfecting unit 100.

In the endoscope cleaning and disinfecting unit 100 according to the present embodiment, the bottle attaching section 43 has bottle receiving sections 43a which receive the closed off mouth sections 51a of the bottles 50A and 50B holding a concentrated disinfectant solution in a watertight and airtight manner; an inlet 43c for guiding the concentrated disinfectant solution into the disinfectant solution tank 32; and protruding sections 43b that allow the inside of the bottles 50A and 50B to communicate with the inside of the disinfectant solution tank 32 via the inlet 43c by opening the mouth sections of the bottles which are received by the bottle receiving sections in watertight fashion.

Therefore, before the bottles 50A and 50B holding a concentrated disinfectant solution are attached to the bottle attaching sections 43a, the mouth sections 51a of the bottles 50A and 50B are closed off, and while the bottles 50Ab and 50B are being connected to the bottle attaching sections 43a, the concentrated disinfectant solution in the bottles 50A and 50B can flow into the disinfectant solution tank 32 via the inlet 43c because the inside of the bottles 50A and 50B and the inside of the disinfectant solution tank 32 can communicate with each other in such a manner as to be cut off from the outside. Therefore, when injecting a disinfectant solution into the disinfectant solution tank 32, no vapor of the disinfectant solution can leak out.

In addition, the endoscope cleaning and disinfectant unit 100 according to the present embodiment includes a bottle detecting sensor 62 which can detect the bottles being connected to the bottle attaching section 43a. For this purpose, the concentrated solution is diluted with a diluting solution based on both the information detected by the level sensors 44, 45, and 46, and that detected by the bottle detecting sensor 62. Therefore, when empty bottles 50A and 50B are placed in the bottle receiving sections 43, the level sensor 44 detects the situation so that an exact preparation level can be assured. (Such a situation can be averted as the diluting solution alone is injected into the disinfectant solution tank 32.) Moreover, even though bottles 50A and 50B are put in place before the disinfectant solution tank 32 is emptied, the level sensor 44 detects the situation so that a disinfectant solution of different concentration from the predetermined can be prevented from being supplied to the cleaning tank 1.

In the present embodiment, the bottle section 50 can be attached to the disinfectant solution tank 32 from a side of the unit. Therefore, the entire unit may be reduced in size.

In the present embodiment 100, the mouth sections 51a of the bottles 50A and 50B are eccentric to the center axis of the bottle body 51, and the bottle receiving sections 43a of the bottle attaching sections 43 are located at a lower part in the bottle insertion hole 63. That is, when the mouth sections 51a of the bottles 50A and 50B are placed in the bottle insertion hole 63 with the mouth sections 51a down as shown in FIG. 2, the mouth sections 51a (caps 52) can be attached to the bottle receiving sections 43a, while when the mouth sections 51a of the bottles 50A and 50B are placed in the bottle insertion hole 63 with the mouth sections 51a up, the mouth sections 51a (caps 52) cannot be attached to the bottle receiving sections 43a. Accordingly, the bottle section 50 is prevented from being reversibly inserted.

Although in the present embodiment, the bottle detecting sensor 62 is a contact-sensor, the bottle detecting sensor 62 may be a photo-sensor.

Additional advantages and modifications will readily occurs to those skilled in the art. Therefore, the invention in its broader aspects is not limited to the specific details and representative embodiments shown and described herein.

Accordingly, various modifications may be made without departing from the spirit or scope of the general inventive concept as defined by the appended claims and their equivalents.

What is claimed is:

1. An endoscope cleaning and disinfecting unit including a cleaning tank in which an endoscope to be cleaned is placed, a disinfectant solution tank in which a disinfectant solution to be supplied is held, and a disinfectant solution duct, connecting said disinfectant solution tank to said cleaning tank, through which a disinfectant solution flows between said cleaning tank and said disinfectant solution tank, said endoscope cleaning and disinfecting unit comprising:

an inlet arranged on said disinfectant solution tank through which a concentrated disinfectant solution is injected into said disinfectant solution tank;

a diluting solution supply for supplying a diluting solution for diluting said concentrated solution to said disinfectant solution tank;

a plurality of level sensors which detect the quantity of the disinfectant solution held in said disinfectant solution tank in stages; and a control section for controlling said diluting solution supply based on the information detected by said level sensors to dilute said concentrated solution injected into said disinfectant solution tank through said inlet to a predetermined concentration.

2. An endoscope cleaning and disinfecting unit according to claim 1, and further including a bottle detector to detect a bottle being connected to said inlet.

3. An endoscope cleaning and disinfecting unit according to claim 2, wherein said control section controls said diluting solution supply based on information detected by said bottle detector and said level sensors.

4. An endoscope cleaning and disinfecting unit according to claim 1, and further comprising a lock for preventing a bottle connected to a bottle attaching section from coming off from said bottle attaching section.

5. An endoscope cleaning and disinfecting unit according to claim 2, and further comprising a lock for preventing said bottle connected to a bottle attaching section from coming off from said bottle attaching section.

6. An endoscope cleaning and disinfecting unit according to claim 3, and further comprising a lock for preventing said bottle connected to a bottle attaching section from coming off from said bottle attaching section.

7. An endoscope cleaning and disinfecting unit including a cleaning tank in which an endoscope to be cleaned is placed, a disinfectant solution tank in which a disinfectant solution to be supplied is held, and a disinfectant solution duct connecting said disinfectant solution tank to said cleaning tank through which the disinfectant solution flows between said cleaning tank and said disinfectant solution tank, said disinfectant solution tank comprising:

an inlet for guiding a concentrated disinfectant solution into said disinfectant solution tank;

a bottle attaching section having a bottle receiving section for detachably receiving a closed mouth section of a bottle holding said concentrated disinfectant solution, and—communicating said mouth section to said inlet in a watertight and airtight manner when said bottle is received by said receiving section, a sealing section adapted to seal between said inlet and said mouth section of said bottle in a watertight and airtight manner when said bottle is received by said receiving section; and an opening device adapted to open said bottle by breaking said closed mouth section thereof when said bottle is received by said bottle receiving section such that said sealing section connects said mouth section to said inlet in a watertight and airtight manner.

8. An endoscope cleaning and disinfecting unit according to claim 7, and further including a bottle detector to detect said bottle being connected to said bottle attaching section.

9. An endoscope cleaning and disinfecting unit according to claim 8, and further comprising a lock for preventing said bottle connected to said bottle attaching section from coming off from said bottle attaching section.

10. An endoscope cleaning and disinfecting unit according to claim 5, and further comprising a lock for preventing said bottle connected to said bottle attaching section from coming off from said bottle attaching section.

11. An endoscope cleaning and disinfecting unit including a cleaning tank in which an endoscope to be cleaned is placed, a disinfectant solution tank in which a disinfectant solution to be supplied is held, and a disinfectant solution duct connecting said disinfectant solution tank to said cleaning tank through which the disinfectant solution flows between said cleaning tank and said disinfectant solution tank, said endoscope cleaning and disinfecting unit comprising:

a bottle attaching section having a bottle receiving section which receives a closed mouth section of a bottle holding a concentrated disinfectant solution in a watertight and airtight manner;

an inlet for guiding the concentrated disinfectant solution into said disinfectant solution tank; and a passage that allow the inside of said bottle to communicate with the inside of said disinfectant solution tank via said inlet by opening said mouth section of said bottle which is received by said bottle receiving section in a watertight and airtight manner, a diluting solution supply for supplying a diluting solution for diluting said concentrated solution to said disinfectant solution tank, a plurality of level sensors which detect the quantity of the disinfectant solution held in said disinfectant solution tank in stages; and a control section for controlling said diluting solution supply based on the information detected by said level sensors to dilute said concentrated solution injected into said disinfectant solution tank through said inlet to a predetermined concentration.

12. An endoscope cleaning and disinfecting unit according to claim 11, and further including a bottle detector to detect said bottle being connected to said bottle attaching section.

13. An endoscope cleaning and disinfecting unit according to claim 11, and further comprising a lock for preventing said bottle connected to said bottle attaching section from coming off from said bottle attaching section.

14. An endoscope cleaning and disinfecting unit according to claim 12, wherein said control section controls said diluting solution supply based on information detected by said bottle detector and said level sensors.

15. An endoscope cleaning and disinfecting unit according to claim 12, and further comprising a lock for preventing said bottle connected to said bottle attaching section from coming off from said bottle attaching section.

16. An endoscope cleaning and disinfecting unit according to claim 14, further comprises a lock for preventing said bottle connected to said bottle attaching section from coming off from said bottle attaching section.

17. An endoscope cleaning and disinfecting unit including a cleaning tank in which an endoscope to be cleaned is placed, a disinfectant solution tank in which a disinfectant solution to be supplied is held, and a disinfectant solution duct connecting said disinfectant solution tank to said cleaning tank through which a disinfectant solution flows between said cleaning tank and said disinfectant solution tank, said disinfectant solution tank comprising:

an inlet for guiding the concentrated disinfectant solution into said disinfectant solution tank;

a bottle attaching section having a bottle receiving section for detachably receiving a closed mouth section of a bottle holding said concentrated disinfectant solution, and communicating said mouth section to said inlet in a watertight and airtight manner when said bottle is received by said receiving section;

a sealing section adapted to seal between said inlet and said mouth section of said bottle in a watertight and airtight manner when said bottle is received by said receiving section; and an opening device adapted to open said bottle by breaking said closed mouth section thereof when said bottle is received by said bottle receiving section such that said sealing section connects said mouth section to said inlet in a watertight and airtight manner;

a diluting solution supply for supplying a diluting solution for diluting said concentrated solution to said disinfectant solution tank;

a bottle detector for detecting said bottle being connected to said bottle attaching section;

a control section for controlling said diluting solution supply based on the information detected by said bottle detector to dilute said concentrated solution injected into said disinfectant solution tank through said inlet to a predetermined concentration.

18. An endoscope cleaning and disinfecting unit according to claim 1, wherein said plurality of level sensors including a first and second level sensors, in which said first level sensor is arranged to detect a first predetermined amount of said concentrated disinfectant solution supplied in said disinfectant solution tank and said second level sensor is arranged to detect a second predetermined amount of said dilution liquid supplied in said disinfectant solution; and wherein said control section is adapted to control said dilution liquid supply in such a manner that said dilution liquid supply starts to supply said dilution liquid in said disinfectant solution tank after said first level sensor detects said first predetermined amount of said concentrated disinfectant solution supplied in said disinfectant solution tank, and stops to supply said dilution liquid in said disinfectant solution tank after said second level sensor detects said second predetermined amount of said dilution liquid supplied in said disinfectant solution.

19. An endoscope cleaning and disinfecting unit according to claim 11, wherein said plurality of level sensors including a first and second level sensors, in which said first level sensor is arranged to detect a first predetermined amount of said concentrated disinfectant solution supplied in said disinfectant solution tank and said second level sensor is arranged to detect a second predetermined amount of said dilution liquid supplied in said disinfectant solution; and wherein said control section is adapted to control said dilution liquid supply in such a manner that said dilution liquid supply starts to supply said dilution liquid in said disinfectant solution tank after said first level sensor detects said first predetermined amount of said concentrated disinfectant solution supplied in said disinfectant solution tank, and stops to supply said dilution liquid in said disinfectant solution tank after said second level sensor detects said second predetermined amount of said dilution liquid supplied in said disinfectant solution.

* * * * *

UNITED STATES PATENT AND TRADEMARK OFFICE
CERTIFICATE OF CORRECTION

PATENT NO.     : 6,379,632 B1
DATED          : April 30, 2002
INVENTOR(S)    : Toshiharu Kinoshita et al.

It is certified that error appears in the above-identified patent and that said Letters Patent is hereby corrected as shown below:

<u>Title page,</u>
Item [30], change the Foreign Priority Application number from "11-28863" to
-- 11-28864 --.

Signed and Sealed this

Fifteenth Day of October, 2002

*Attest:*

*Attesting Officer*

JAMES E. ROGAN
*Director of the United States Patent and Trademark Office*